United States Patent [19]

Chinnock et al.

[11] Patent Number: 4,969,450

[45] Date of Patent: Nov. 13, 1990

[54] VIDEOARTHROSCOPE WITH ONE-HANDED CONTROL

[75] Inventors: Randal B. Chinnock, North Reading, Mass.; Arthur Shoemaker, Syosset, N.Y.

[73] Assignee: Smith & Nephew Dyonics, Inc., Andover, Mass.

[21] Appl. No.: 470,297

[22] Filed: Jan. 25, 1990

[51] Int. Cl.[5] .............................................. A61B 1/04
[52] U.S. Cl. ..................................................... 128/6
[58] Field of Search ........................... 128/4, 6; 358/98

[56] References Cited

U.S. PATENT DOCUMENTS

| | | | |
|---|---|---|---|
| 4,590,923 | 5/1986 | Watanabe | 128/6 |
| 4,611,888 | 9/1986 | Prenovitz et al. | 128/6 X |
| 4,722,000 | 1/1988 | Chatenever | 128/6 X |
| 4,756,304 | 7/1988 | Watanabe | 128/6 |
| 4,807,594 | 2/1989 | Chatenever | 128/4 |
| 4,844,071 | 7/1989 | Chen et al. | 128/6 |
| 4,854,302 | 8/1989 | Allred, III et al. | 128/6 |

*Primary Examiner*—William H. Grieb
*Attorney, Agent, or Firm*—Kirkpatrick & Lockhart

[57] ABSTRACT

The present invention provides a videoarthroscope which is longitudinally compact so tht it can be held and controlled with one hand. the videoarthroscope of the present invention includes a needle assembly and a focusing assembly rotatable relative to each other to permit rotation of the needle tip. The focusing assembly includes a rotatable focusing ring. All confronting rotating surfaces are sealed by a multilobed seal and provided with a lubricant to promote both ease of movement and sealing of movable joints. The videoarthroscope includes in its optical assembly a movable focusing group comprised of two lenses and an optional fixed telescope lens.

18 Claims, 4 Drawing Sheets

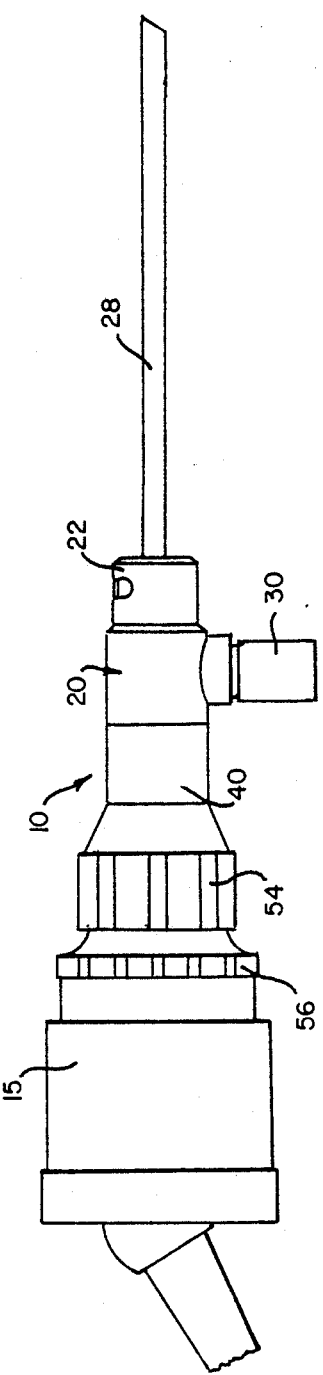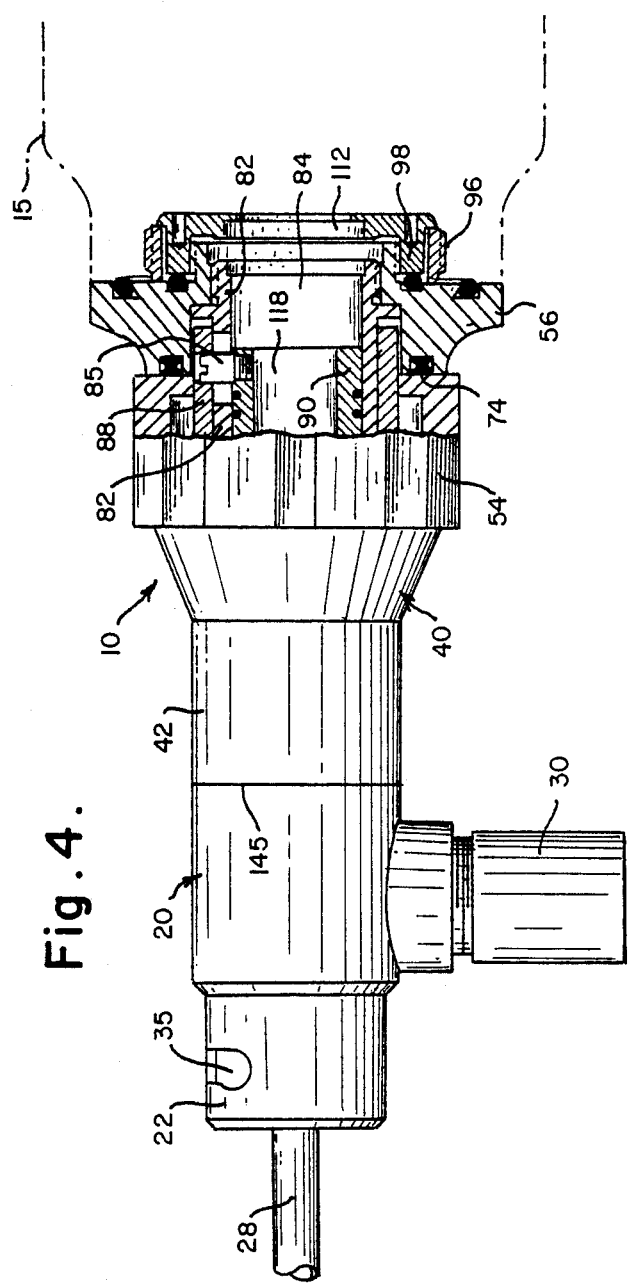

VIDEOARTHROSCOPE WITH ONE-HANDED CONTROL

BACKGROUND OF THE INVENTION

1. Field of the Invention

The present invention relates to videoarthroscopes.

2. Description of the Prior Art

The field of arthroscopic surgery has progressed rapidly. It has significantly changed the way in which orthopaedic surgeons treat a host of problems.

The earliest arthroscopes used an ocular lens and an eye shade through which the surgeon directly viewed the anatomy by looking into the ocular. As video cameras developed, they became practical for use with arthroscopes. Coupler systems for optically coupling the image from the arthroscope to a video camera were developed. Referring to FIG. 1, the early coupler systems included an arthroscope 2, a coupler 4 and a camera housing 6. The assemblies tended to be relatively bulky and cumbersome. Maneuverability was difficult.

An improved coupler which overcame some of those problems is described in Prenovitz et al., U.S. Pat. No. 4,611,888. The Prenovitz coupler consists of two sections rotatable with respect to one another. The front section of the coupler is nonrotatably mounted to the proximal end of an arthroscope. The rear section of the coupler is nonrotatably mounted to the distal end of a video camera. Rotation of the arthroscope image with respect to the camera is effected by rotating the front section of the coupler with respect to its rear section. Because of the two-piece construction of the coupler, seals are needed between the arthroscope and the front section of the coupler, between the rear section of the coupler and the camera, and between the front and rear sections of the coupler itself.

Other patents relating to video arthroscopes include Watanabe, U.S. Pat. Nos. 4,590,923 and 4,756,304.

Later, videoarthroscopes were developed which combine the functions of the arthroscope and the coupler, as shown in FIG. 2. The videoarthroscope 8 attaches directly to the camera housing 15.

During arthroscopic surgery, the surgeon uses one hand to remove, repair or dress tissue with instruments such as probes, knives, forceps and cutters. With the other hand, the surgeon holds the videoarthroscope. Arthroscopes can be focused to accommodate changes in the distance of the observed surface. The angular needle of the arthroscope can also be rotated about its longitudinal axis to scan the operative area and thereby increase the field of view. The focusing and rotation adjustments are critical.

The size and configuration of the arthroscope-coupler-camera assemblies and videoarthroscopes have, heretofore, required the surgeon to use two hands to make those critical adjustments. The prior art devices are relatively long (FIGS. 1, 2 and 3 are drawn to full scale) and have a high degree of rotational stiffness in their focusing and rotation means. Thus, they cannot be held in one's hand and adjusted with the fingers of that same hand. In order to make the necessary adjustments, the surgeon must let go of the cutting or probing instrument to free both hands for maneuvering the videoarthroscope. He must then reposition the cutting or probing instrument to resume the procedure. The practice is not only time consuming but lends itself to error.

There is a need for a videoarthroscope which can be held and maneuvered with one hand. An object of the present invention is to provide a videoarthroscope which permits one handed control.

SUMMARY OF THE INVENTION

The present invention provides a videoarthroscope with one-hand control. It is longitudinally compact and easy to maneuver. The videoarthroscope of the present invention includes a needle assembly and a focusing assembly. The focusing assembly is mountable in use at the proximal end thereof, in a sealed relationship, to a video camera and secured at the distal end thereof, in a sealed relationship, to the needle assembly. The needle assembly and the focusing assembly are aligned along a common axis. The needle assembly is rotatable about the axis relative to the focusing assembly at a rotating joint to rotatably orient the needle assembly with respect to the video camera. The videoarthroscope also includes an optical assembly which includes a focusing group preferably comprised of a first lens means and a second lens means and rotatable means in a confronting relationship to surfaces of the focusing assembly for axially moving the focusing group. The needle assembly and the focusing assembly are configured to permit the videoarthroscope to be held and controlled in use in one hand.

The videoarthroscope may also include in the optical assembly a third lens means, preferably a fixed telescope lens rearward of the focusing group and proximate the proximal end of the focusing assembly. First sealing means are preferably provided for effecting a moisture tight seal between the needle assembly and the focusing assembly and between the rotatable moving means and confronting surfaces of the focusing assembly. The first sealing means are configured to provide a pocket for receiving lubricant to reduce the rotational stiffness of the various rotating members. Second sealing means are also preferably provided between the focusing assembly and the video camera.

BRIEF DESCRIPTION OF THE DRAWINGS

The present invention can be better understood by reference to the drawings in which:

FIG. 3 is a side elevation view of the videoarthroscope with one hand control of the present invention coupled to a camera housing drawn to full scale;

FIG. 4 is an enlarged side elevation partial section view of the videoarthroscope of FIG. 3;

DETAILED DESCRIPTION OF THE PREFERRED EMBODIMENTS

The videoarthroscope 10 of the present invention is illustrated in FIGS. 3–6.

Figure 1:
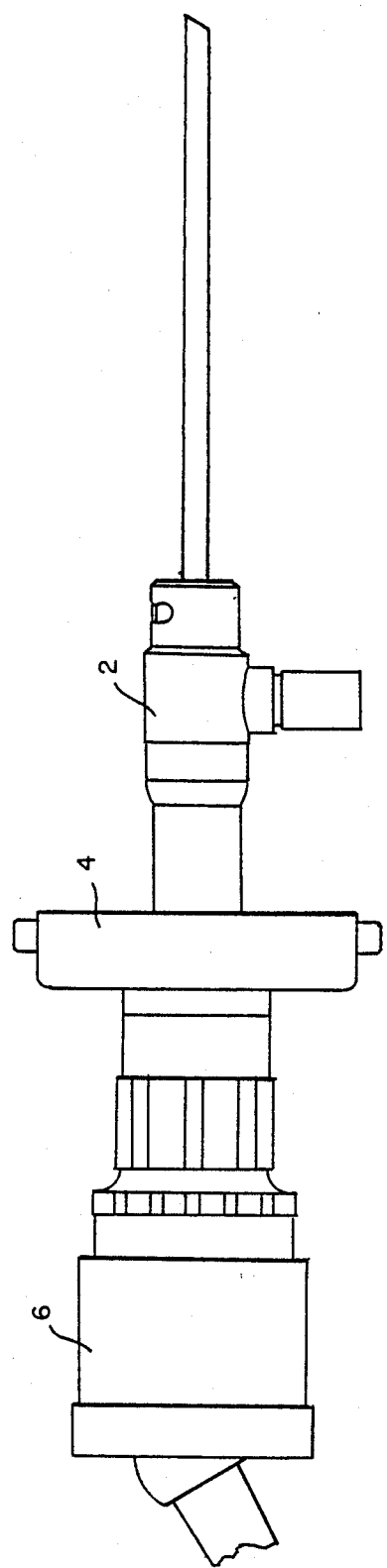
FIG. 1 is a side elevation view of a prior art arthroscope-coupler-camera assembly drawn to full scale.
Figure 2:
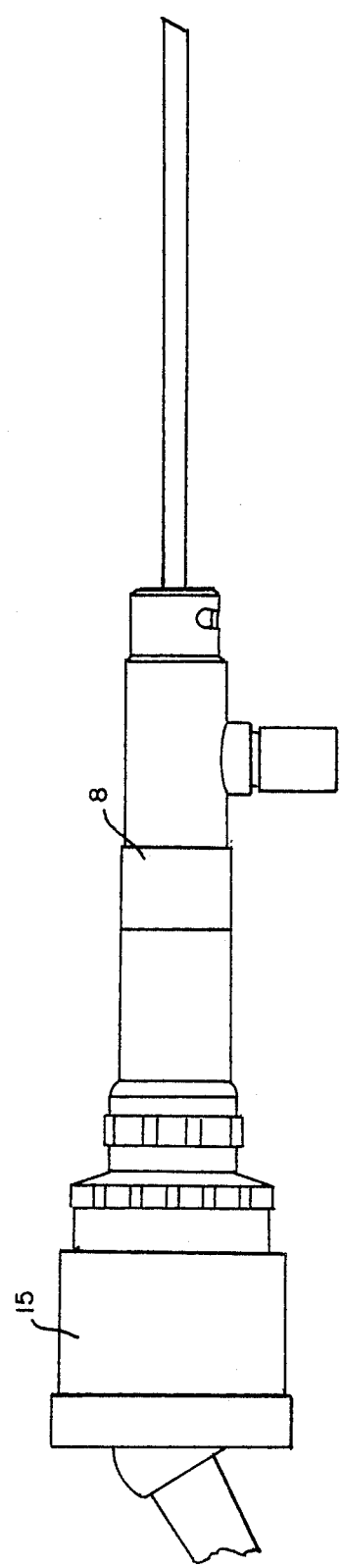
FIG. 2 is a side elevation view of a prior art videoarthroscope and camera drawn to full scale.

Comparing FIG. 3 to FIGS. 1 and 2, it is apparent that videoarthroscope 10 is longitudinally compact relative to the prior art devices. The reduction in length is one feature of videoarthroscope 10 which permits true one handed control. "Hand" as used herein shall mean an adult human hand. In the preferred embodiment, the videoarthroscope 10 is sized to be held and controllable by hands falling within about the 95th percentile of large and small adult human hands.

In addition to the reduction in length, the rotational torque of various components has been reduced by means which will be described more fully hereinbelow so that movement can be achieved by two or three fingers of the hand holding the videoarthroscope. Finally, a complex optical assembly was designed to accommodate the shorter optical track of the longitudinally compact videoarthroscope without sacrificing focusing ability, clarity and depth of field.

As seen clearly in FIG. 3, the videoarthroscope 10 of the present invention includes a needle assembly 20 and a focusing assembly 40 which are rotatable relative to each other at rotation joint 145. The proximal end of the focusing assembly 40 can be releasably secured to any of the video cameras typically used in arthroscopy. FIGS. 3 and 4 illustrate the position of a video camera 15 when mounted on the rear portion of videoarthroscope 10.

Figure 5:
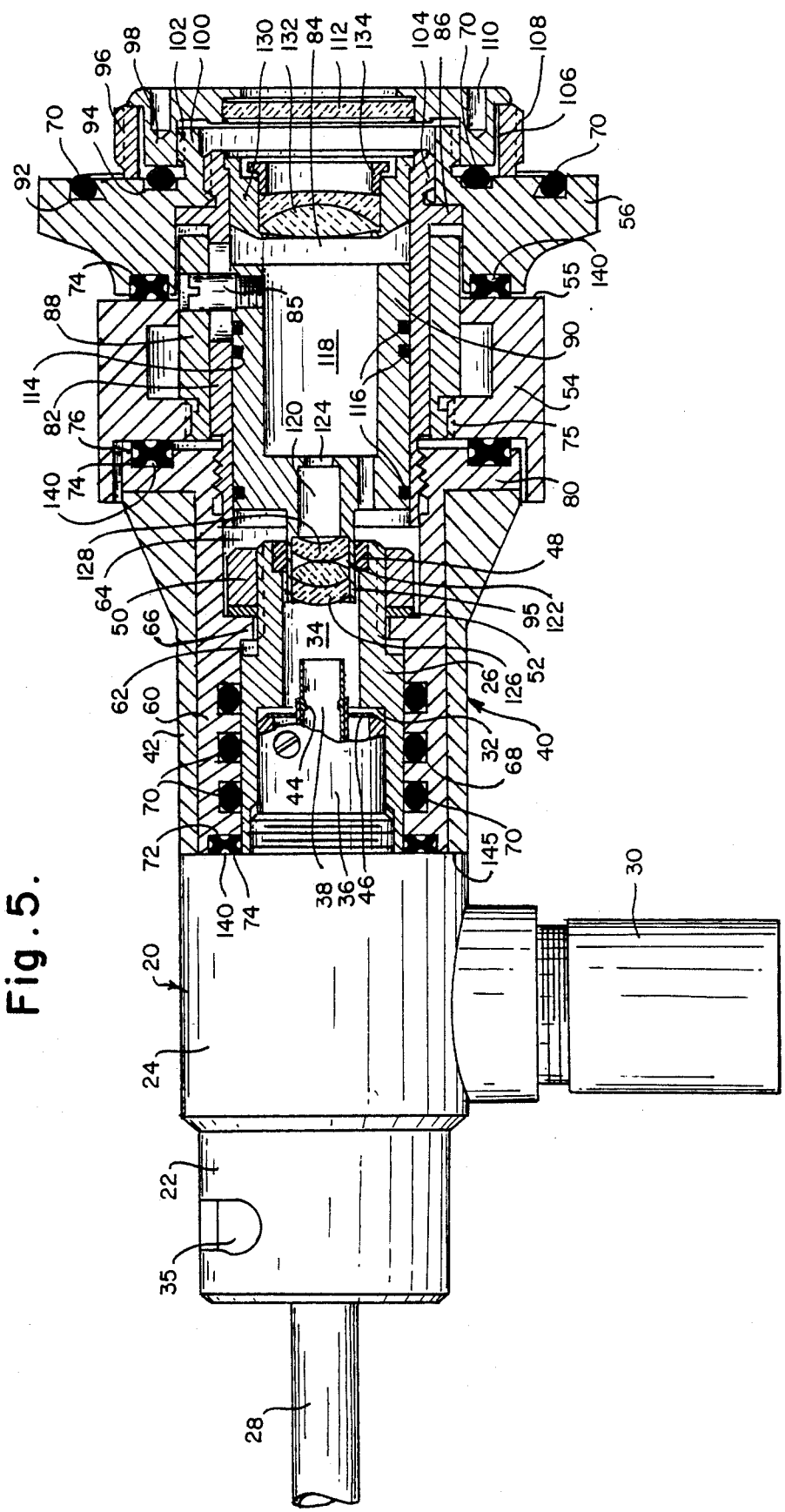
FIG. 5 is an enlarged side elevation partial section view of an alternative embodiment of the videoarthroscope of FIG. 3.
Figure 6:
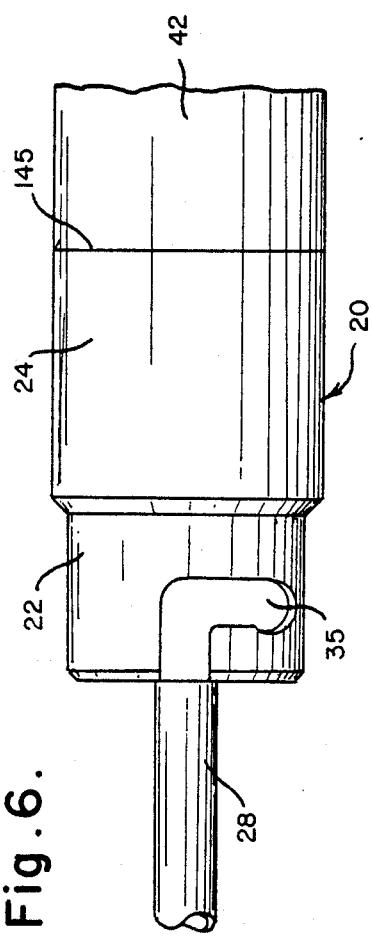
FIG. 6 is an enlarged side elevation view of a portion of the videoarthroscope of FIGS. 3, 4 or 5, rotated 90°.

Referring to FIG. 5, the needle assembly 20 includes a front portion 22, a mid portion 24 and a shank 26. The needle 28 extends distally from the front portion 22. A light guide post 30 is provided on mid portion 24 to receive light for the videoarthroscope 10. An elbow shaped groove 35 is provided on the surface of front portion 22, as shown in FIG. 6, to lock accessory instruments into position over needle 28.

The shank 26 is received into, and is rotatable on a bearing surface of the focusing assembly 40. The shank 26 includes a proximal bore 34 with a counter bore 32. The neck 36 of mid portion 24 extends into counter bore 32. An optical tube or rod 38 extends through a ring 46 in the opening of the neck 36. A low friction sleeve 48 is seated at the opening of bore 34 in the shank 26. A nut 50 and low friction thrust washer 52 are preferably provided to retain the shank 26 within the distal end of the focusing assembly 40. However, those skilled in the art will recognize that any suitable fastening means which will permit rotation of needle assembly 20 while securing shank 26 within the focusing assembly 40 will suffice. The nut 50 is secured to the shank 26 by threads. There is a field stop 44 in the form of a sharp edge in the interior of the optical tube or rod 38. The arthroscopic image appears in the plane of the field stop. That plane defines one end of the optical track. The other end is defined by the plane of the camera chip, or CCD (not shown). The optical track will be discussed in more detail hereinbelow in connection with the optical assembly used in the videoarthroscope 10 of the present invention.

The focusing assembly 40 includes, from the distal end to the proximal end, on the surface, a front portion 42, a focusing ring 54 and a rear portion 56. The distal end of front portion 42 abuts mid portion 24 of needle assembly 20 to define a rotational joint 145. Rotation of the needle assembly 20 relative to the focusing assembly 40 at joint 145 rotates the tip of needle 28 to scan the field and increase the size of the field of view. Rear portion 56 abuts the video camera housing 15 (shown in FIGS. 3 and 4) when the camera is connected to the videoarthroscope 10.

On the interior of the focusing assembly 40, there is an interior bearing surface or sleeve 60, a lens body 82, a lens cell 90 and a focusing sleeve 88. The front portion 42 is hollow and surrounds interior sleeve 60. Sleeve 60 is also hollow and includes a distal bore 62 which is separated by an interior ring 66 from a proximal bore 64. Distal and proximal bores 62, 64 receive the shank 26 of the needle assembly 20. Ring 66 provides a stop for the nut 50 and washer 52 to secure shank 26 within bores 62, 64. There are shown three radial grooves 68 cut into the interior of distal bore 62. Each groove 68 seats an O-ring seal 70. The O-rings 70 provide a means for adjusting the rotational torque or stiffness of the needle assembly relative to the focusing assembly. By decreasing the number of O-rings 70, the torque is reduced. By increasing them, the torque is increased.

The interior sleeve 60 also includes seats 72 and 76 at its distal and proximal ends, respectively, for receiving lowdrag multilobed elastomer seals 74. The seals 74 are preferably somewhat X-shaped and have crescent shaped pockets 140 between the four lobes. A lubricant is applied to the pockets to promote ease of movement while enhancing the sealing function. Seat 76 and a seal 74 are positioned in a flange 80 which radiates outwardly from interior sleeve 60. Flange 80 abuts, on one side, the proximal end of front portion 42. On the other side of flange 80, the seal 74 rests in seat 76 and abuts, in a sealed relationship, the distal face of focusing ring 54. Seat 72 and a seal 74 abut the proximal end of mid portion 24 to provide a seal at rotational joint 145.

Lens body 82 is hollow and includes bore 84 and a flange 86 at its rear end. Threads are provided at the opening of proximal bore 64 to engage the threads of the lens body 82. Lens body 82 is surrounded by focusing sleeve 88. A cam screw 85 secures the lens body 82, focusing sleeve 88 and lens cell 90 together.

The focusing sleeve 88 is surrounded by the focusing ring 54 and secured to it by threads 75, as shown, or by any other suitable known means. A lip on focusing ring 54 loosely surrounds flange 80 and the proximal end of front portion 42. The proximal face of focusing ring 54 abuts the distal face of the rear portion 56 of focusing assembly 40 in a sealed relationship. A seat 55 and multilobed seal 74 in rear portion 56 provide the seal. The proximal face of the rear portion 56 includes two grooves 92 and 94 to seat O-ring seals 70.

Lens cell 90 includes outward radial grooves 114 for seating O-rings 116, a proximal bore 118, a mid bore 120 and a distal bore 122. O-rings 116 provide a means for eliminating the "play" between lens cell 90 and lens body 82 which, if permitted, can cause the image to wander on the viewing monitor. An aperture stop 124 permits light to pass through to the proximal bore 118 while rejecting stray light, thereby improving contrast. The distal bore 122 seats the two focus group lenses, 126 and 128, in a precise position relative to the field stop 44 and allows axial movement sufficient to obtain focus over a wide range of object distances. Rearward of the lens cell 90 is the lens mount 130 which seats an optional third lens 132 and a retainer 134. The optical design of the videoarthroscope 10 of the present invention will be explained in further detail hereinbelow.

A thread ring 96 and a locking ring 98 are positioned on the proximal face of rear portion 56. Locking ring 98 abuts the seal 70 seated in groove 94 and is secured to the neck 100 of rear portion 56 by threads 102 and 104. Thread ring 96 is held in place by locking ring 98. As can be seen by reference to FIG. 5, a space 106 is provided between thread ring 96 and locking ring 98 to permit radial movement of thread ring 96. Threads 108 on the exterior of thread ring 96 and bores 110 in locking ring 98 provide means for mounting camera housing 15 to videoarthroscope 10. A window 112 is provided in locking ring 98 to pass the image from the videoarthroscope to the camera. A similar window is generally provided in the camera housing.

An advantage of the videoarthroscope 10 of the present invention is the ease with which the rotatable parts can be rotated. In order to make one handed control feasible, focusing and rotation of the image must be able to be performed by using only two or three fingers, without a great deal of exertion. The torque required to rotate the needle assembly 20 relative to the focusing assembly 40 at joint 145 and the focusing ring 54 is reduced significantly as compared to prior art devices. The combination of the multilobed seals 74, the lubricant dispersed in the crescent-shaped pockets 140 between the lobes of the seals 74 and the polished surface finishes of the contacting surface reduces rotational stiffness while providing excellent sealing properties. The multilobed seals 74 are made of ethylene propylene. The lubricant is a high vacuum grease of a type commercially available from Dow Corning Corporation. The grease is a stiff, nonmelting silicone material that is nonoxidizing, nongumming, water resistant and has good chemical and thermal stability sufficient to withstand the high temperature, pressure and vacuum environments present in steam and chemical sterilization systems. Sealing compounds employed heretofore have had a tendency to swell over time, increasing rotational stiffness to unacceptable levels. The high vacuum silicone grease used in the present invention has not been found to demonstrate the same tendency.

In addition, the nut 50 and low friction washer 52 hold the videoarthroscope 10 together with little increase in rotational stiffness while providing high lateral stiffness to maintain the image position on the camera chip or CCD. The washer is preferably made from a polyamide plastic.

The sleeve 48 disposed between the neck 95 of the lens cell 90 and the opening of bore 34 of shank 26 of the needle assembly 20 is preferably made of a fluoro polymer such as PTFE or a material having comparable low surface tension properties. The neck 95 moves axially against the sleeve 48 with ease to eliminate decentration of the image on the monitor while not increasing significantly the force required to move lens cell 90.

O-ring seals 70 positioned in grooves 68 of the interior sleeve 60 of the focusing assembly 40, as stated above, may vary in number (three are shown) and are used to adjust the torque or rotational stiffness as required.

The optical design of the videoarthroscope 10 provides a significant improvement over prior art videoarthroscopes. Conventional videoarthroscopes typically employ a single lens, which may be either a singlet or a doublet, between the field stop and the CCD. When the lens is moved axially to focus the arthroscopic image, the magnification changes significantly. In surgery, the constant change can be quite bothersome. In order to change the overall magnification of the system, a different arthroscope having a lens of a different magnification was required. There has heretofore been no commonality of parts in providing lenses of different magnifications.

The optical assembly of the videoarthroscope 10 includes at least two lenses, preferably a chromatically corrected doublet 126 and a second correcting lens 128, which together comprise the focusing group. The correcting lens is preferably of a meniscus or other shape, such as plano convex, plano concave or convex. The doublet 126 is made in a manner known in the art from flint and crown glass, glued together.

A third lens may be provided, preferably a telescope lens 132 as shown in FIG. 5. FIG. 4 illustrates the embodiment of videoarthroscope 10 without a third lens 132, a retainer 134, or a lens mount 130. All other aspects of the videoarthroscopes shown in FIGS. 4 and 5 are the same. The telescope lens 132 is a doublet and remains in a fixed position within the lens mount 130 of a particular videoarthroscope 10. Only the focusing group moves axially within a videoarthroscope 10. When the telescope lens 132 is used, the change in magnification attributable to axial movement of the focusing group is substantially eliminated. The use of the telescope lens 132 provides the advantages of an infinity corrected optical system similar to that used in television cameras and microscopes, but not heretofore used in videoarthroscopes. For practical purposes, the infinity corrected system means that there is no change in the size of the image on the monitor screen when focusing.

In making the videoarthroscope 10 longitudinally compact so that it can be held and controlled by one hand, the optical track, the distance between the field stop 44 and the camera chip or CCD, was reduced in the preferred embodiment to about 50 mm. Reducing the optical track in optical design presents a variety of problems, including the use of glasses of high indices of refraction and curved surfaces of small radii, which had to be overcome in developing the videoarthroscope 10 of the present invention.

Those problems were overcome by the addition of the second lens in the focusing group. The correcting lens 128 corrects aberrations, or imperfections in the image. The meniscus 128 reduces field curvature which, in a perceptual sense, increases the depth of field of the optical system. An improved depth of field is important in arthroscopy where the observed features are not all in the same plane.

The addition of the telescope lens 132 also reduces manufacturing costs with respect to the tolerances of the components. Without a telescope lens, the optical system is more sensitive to certain kinds of decentration of the image. In order to maintain an image in the center of the monitoring screen throughout the focus range of the videoarthroscope, everything along the optical axis must be centered relative to the CCD in the camera. If not centered, the image moves around on the screen during focusing. The presence of telescope lens 132 corrects the off center image so that its appearance on the monitor is substantially centered. All exposed lens and window surfaces of the videoarthrosoope 10 and camera 15 are preferably coated with a high efficiency multi-layer antireflective material to reduce the reflectivity of the optic surfaces, thus increasing brightness and contrast of the image. The glass used for the lenses preferably has a refractive index of about 1.43 to about 1.85.

The final alignment of the center of the CCD to the optical axis of the videoarthroscope during manufacture is provided by the radially movable thread ring 96. The thread ring 96 screws onto the camera so that the CCD is centered relative to the longitudinal axis of the thread ring 96. If the CCD is not centered relative to the optical axis of videoarthroscope 10, the thread ring 96 can be moved radially relative to the videoarthroscope 10 to align the center of the CCD with the optical axis. An uncured but fast curing adhesive is applied to the thread ring 96 and the space 106 so that the thread ring can be secured in the desired position.

The optical design of the videoarthroscope 10 permits a commonality of features among different magnification sizes offered. For example, the first lens 126 of the focusing group may be the same in all sizes, while the magnification of the correcting lens 128 or the presence and the magnification of the third lens 132 may vary.

Those skilled in the art will appreciate that the precise magnification and radii of the lenses and their relative positions along the optical track will vary depending upon factors such as exact track length, needle size, camera chip or CCD size, diameter of the field stop and desired magnification of the system as a whole.

A preferred design for the videoarthroscope 10 has a length of about 7.2 cm from the window 112 to the distal face of front portion 22. The optical system for a videoarthroscope 10 of that size employing a 50.00 mm track length and a magnification of 4.0×, a needle size of 4.0 mm, a camera chip format of two thirds inch, a window thickness of about 1.6 mm and a field stop diameter of 1.83 mm may successfully employ a focusing group positioned about 6.8 mm from the plane of the field stop to the vertex of the doublet and about 4.5 mm from the vertex of the meniscus to the aperture stop and a telescope lens whose distal vertex is in a plane positioned about 29.1 mm from the plane of the CCD.

By varying the size of the CCD or the desired magnification of the videoarthroscope as a whole, the relative positions of the lenses along the track would change as well. For example, by changing the magnification in the above example from 4.0× to 3.0× and the CCD format to one-half inch, the position of the plane of the distal vertex of a telescope lens would be changed to about 22.4 mm from the plane of the CCD. By altering the window thickness or by removing of the window in the videoarthroscope or the camera housing, the relative distance of a telescope lens to the plane of the CCD will also have to be changed to provide the optimum optic conditions. By using optical design skills known in the art, the desired combination of variables can be determined.

Figure 7:
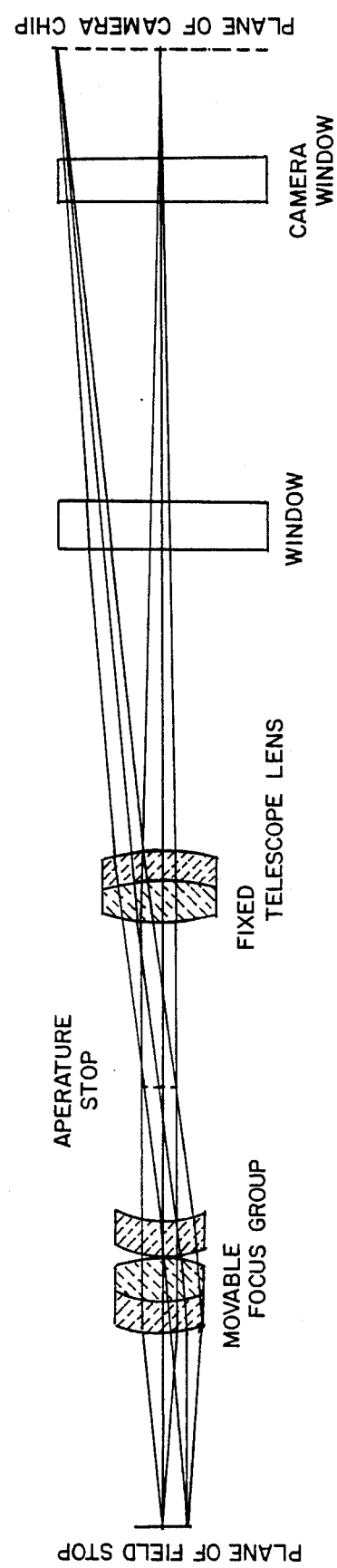
FIG. 7 is a graph of a preferred optical system used in the videoarthroscope of FIG. 5.

FIG. 7 illustrates the optical system of the embodiment of the videoarthroscope 10 described above. The relative positions of the lenses on the optical track are shown. In the focusing group, the distal face of the distal lens in the doublet has a radius of about 6.36 mm. The proximal face of the proximal lens of the doublet has a radius of about −7.56 mm. The radius of the distal face of the proximal lens is about 2.97 mm. The center thickness is about 2.5 mm. The radius of the distal face of the meniscus is about 3.61 mm. The radius of the proximal face of the meniscus is about 3.46 mm. The center thickness is about 1.2 mm. The distance that the focusing group can be moved axially to focus the videoarthroscope 10 is shown in FIG. 7.

In operation, the videoarthroscope 10 shown in FIG. 3 is held in the palm of one hand. The image can be rotated by pushing the post 30 with the thumb and/or index finger of the hand holding the videoarthroscope 10 to rotate needle assembly 20 relative to focusing assembly 40 at joint 145. The image can be focused by rotation of the focusing ring 54 between the thumb and index or middle finger of the hand holding the videoarthroscope 10. Rotation of focusing ring 54 translates to axial movement of the lens cell 90 and the focusing group. The one hand control of videoarthroscope 10 frees the surgeon's other hand.

Those skilled in the art will recognize that although the present invention has been described in terms of a videoarthroscope, the scope of the invention extends to endoscope technology in general.

What is claimed is:

1. A videoarthroscope for use with a video camera comprising:
    a needle assembly;
    a focusing assembly mountable in use at the proximal end thereof in a sealed relationship to a video camera and secured at the distal end thereof in a sealed relationship to said needle assembly, said needle assembly and said focusing assembly being aligned along a common axis, said needle assembly being rotatable about said axis relative to said focusing assembly to rotatably orient said needle assembly with respect to the video camera;
    an optical assembly coaxial to said common axis having a focus group comprised of a first lens means and a second lens means; and
    rotatable means in confronting relationship to surfaces of said focusing assembly for axially moving said focus group;
    said needle assembly and said focusing assembly being configured to permit said videoarthroscope to be held and controlled in use in one hand.

2. The videoarthroscope recited in claim 1 further comprising:
    first sealing means for effecting a moisture tight seal between said needle assembly and said focusing assembly and between said rotatable moving means and confronting surfaces of said focusing assembly.

3. The videoarthroscope recited in claim 2 wherein said first sealing means are configured to define pockets for receiving a lubricant for reducing rotational stiffness while enhancing the moisture tight seal.

4. The videoarthroscope recited in claim 3 wherein said first sealing means is a multilobed elastomer ring having one said pocket defined between two adjacent lobes of said ring.

5. The videoarthroscope recited in claim 2 wherein said focusing assembly further comprises a front portion and a rear portion having said rotatable moving means disposed in a confronting sealed relationship therebetween;
    said front portion, said rotatable moving means and said rear portion being aligned along said common axis and said rotatable moving means being rotatable relative to said front and rear portions; and
    said first sealing means are disposed between said front portion and said rotatable moving means and between said rear portion and said rotatable moving means.

6. The videoarthroscope recited in claim 1 further comprising second sealing means disposed at the proximal end of said focusing assembly for effecting a moisture tight seal between said focusing assembly and the video camera.

7. The videoarthroscope recited in claim 1 wherein said optical assembly further comprises a third lens means rearward of said focusing group proximate the proximal end of said focusing assembly.

8. The videoarthroscope recited in claim 1 wherein the video camera has an optical chip disposed therein and said videoarthroscope further comprises a member for mounting the video camera such that the axis of said mounting member is coaxial to the center of the optical chip, said mounting member being movable radially to align the axis of the optical chip with said common axis.

9. The videoarthroscope recited in claim 1 wherein said video camera includes an optical chip and wherein said optical assembly further comprises:
 a field stop disposed in said needle assembly forward of said focusing group for receiving an image through said needle assembly;
 a lens cell disposed in said focusing assembly and housing said focusing group, said lens cell being axially movable relative to said field stop by the rotation of said rotatable moving means;
 means for translating the radial motion of said moving means to the axial motion of said lens cell;
 an aperature stop rearward of said focusing group disposed in said lens cell for passing light therethrough while blocking stray light;
 an optional fixed third lens means rearward of said aperature stop;
 an optical track defined along the axis between the plane of said field stop and the plane of the optical chip, said optical track being coaxial to said common axis of said needle assembly and said focusing assembly.

10. The videoarthroscope recited in claim 9 wherein said optical track is about 50 mm in length.

11. The videoarthroscope recited in claim 1 wherein said first lens means is a doublet, said second lens means is a correcting lens for correcting abberations of the image and said third lens means is a telescope lens.

12. The videoarthroscope recited in claim 1 further comprising means to adjust the rotational torque of said needle assembly relative to said focusing assembly.

13. The videoarthroscope recited in claim 12 wherein said needle assembly includes a shank extending from the proximal end thereof, said focusing assembly includes a hollow sleeve for receiving said shank, said sleeve having at least one radial groove disposed therein and said torque adjusting means comprise at least one sealing ring disposed in said at least one radial groove of said sleeve such that said at least one sealing ring abuts said shank.

14. An endoscope for use with a video camera comprising:
 a first assembly;
 a second assembly mountable in use in a sealed relationship at the proximal end thereof to a video camera and rotatably secured in a sealed relationship at the distal end thereof to said first assembly;
 an optical assembly housed in said second assembly;
 rotatable means in confronting relationship to surfaces of said second assembly for focusing said optical assembly;
 first sealing means for effecting a moisture tight seal between said first assembly and said second assembly and between said focusing means and confronting surfaces of said second assembly; and
 second sealing means disposed at the proximal end of said second assembly for effecting a moisture tight seal between said second assembly and the video camera.

15. The endoscope recited in claim 14 wherein said first assembly and said second assembly are configured to permit said endoscope to be held and controlled in use in one hand.

16. The endoscope recited in claim 14 wherein said first sealing means are lubricated to reduce rotational stiffness while enhancing the sealing function.

17. The endoscope recited in claim 14 wherein said optical assembly comprises a focusing group having a first lens means and a second lens means for correcting image abberations.

18. The endoscope recited in claim 17 wherein said optical assembly further comprises a third lens means in a fixed position rearward of said focusing group for substantially eliminating changes in image magnification due to translation of said focusing means for focusing said focusing group.

* * * * *

UNITED STATES PATENT AND TRADEMARK OFFICE
CERTIFICATE OF CORRECTION

PATENT NO. : 4,969,450
DATED : November 13, 1990
INVENTOR(S) : Randal B. Chinnock and Arthur Shoemaker It is certified that error appears in the above-identified patent and that said Letters Patent is hereby corrected as shown below:

In the Abstract, item [57], line 2, delete "tht" and substitute --that-- therefor.

In the Abstract, item [57], line 3, delete "the" and substitute --The-- therefor.

Col. 4, line 17, delete "lowdrag" and substitute --low-drag-- therefor.

Col. 9, line 32, delete "abberations" and substitute --aberrations-- therefor.

Col. 10, line 34, delete "abberations" and substitute --aberrations-- therefor.

Signed and Sealed this

Ninth Day of November, 1993

*Attest:*

BRUCE LEHMAN

*Attesting Officer*     *Commissioner of Patents and Trademarks*

UNITED STATES PATENT AND TRADEMARK OFFICE
CERTIFICATE OF CORRECTION

PATENT NO. : 4,969,450
DATED : November 13, 1990
INVENTOR(S) : Randal B. Chinnock and Arthur Shoemaker It is certified that error appears in the above-identified patent and that said Letters Patent is hereby corrected as shown below:

In the "Abstract", line 2, delete "tht" and substitute --that-- therefor.

In the "Abstract", line 3, delete "the" and substitute --The-- therefor.

Col. 4, line 17, delete "lowdrag" and substitute --low-drag-- therefor.

Col. 9, line 32, delete "abberations" and substitute --aberrations-- therefor.

Col. 10, line 34, delete "abberations" and substitute --aberrations-- therefor.

Signed and Sealed this

Twenty-third Day of November, 1993

Attest:

BRUCE LEHMAN

Attesting Officer     Commissioner of Patents and Trademarks